US012697065B2

(12) United States Patent
Jones et al.

(10) Patent No.: US 12,697,065 B2
(45) Date of Patent: Aug. 4, 2026

(54) MONITORING DEVICE

(71) Applicant: Owlet Baby Care, Inc., Lehi, UT (US)

(72) Inventors: Cory Jones, Orem, UT (US); Branden Sheffield, Saratoga Springs, UT (US); Zack Bomsta, Provo, UT (US)

(73) Assignee: OWLET BABY CARE, INC., Lehi, UT (US)

( * ) Notice: Subject to any disclaimer, the term of this patent is extended or adjusted under 35 U.S.C. 154(b) by 224 days.

(21) Appl. No.: 17/352,072

(22) Filed: Jun. 18, 2021

(65) Prior Publication Data

US 2021/0393202 A1     Dec. 23, 2021

Related U.S. Application Data

(60) Provisional application No. 63/042,511, filed on Jun. 22, 2020, provisional application No. 63/042,203, filed on Jun. 22, 2020.

(51) Int. Cl.
A61B 5/00          (2006.01)
A61B 5/01          (2006.01)
(Continued)

(52) U.S. Cl.
CPC .......... A61B 5/6807 (2013.01); A61B 5/0059 (2013.01); A61B 5/01 (2013.01); A61B 5/14551 (2013.01); A61B 5/6831 (2013.01); A61B 5/7221 (2013.01); A61B 5/02438 (2013.01); A61B 2503/04 (2013.01); A61B 2560/0214 (2013.01); A61B 2560/0252 (2013.01);
(Continued)

(58) Field of Classification Search
CPC ....... A61B 5/6807; A61B 5/0059; A61B 5/01; A61B 5/14551; A61B 5/6804; A61B 5/6831; A61B 5/7221; A61B 2503/04; A61B 2560/0252; A61B 2560/0443; A61B 2562/0271; A61B 5/02438; A61B 5/6844; A61B 5/0205; A61B 2560/0214
See application file for complete search history.

(56) References Cited

U.S. PATENT DOCUMENTS 246,454 A     8/1881     Bruen
1,889,716 A     11/1932     Walker
(Continued)

FOREIGN PATENT DOCUMENTS

CA          2334964 A1     12/1999
CN          101108125 A     1/2008
(Continued)

OTHER PUBLICATIONS

US 2022/0192529 A1, 06/2022, Al-Ali et al. (withdrawn)
(Continued)

*Primary Examiner* — Jennifer Pitrak McDonald
*Assistant Examiner* — Christopher J Mutchler
(74) *Attorney, Agent, or Firm* — Workman Nydegger

(57) ABSTRACT

A monitoring device is disclosed having a band or sock or garment configured to be placed about a portion of a subject. The sock or garment houses a sensing module to measure health parameters of the subject. The sensing module has a sensor assembly that is optimized to detect when the device is not properly situated on the subject in order to minimize false readings and/or to improve the reliability of readings from the device.

18 Claims, 8 Drawing Sheets

(51) Int. Cl.
    *A61B 5/024*         (2006.01)
    *A61B 5/1455*      (2006.01)
(52) U.S. Cl.
    CPC ................ *A61B 2560/0443* (2013.01); *A61B 2562/0271* (2013.01)

(56) References Cited

U.S. PATENT DOCUMENTS

| | | | |
|---|---|---|---|
| 2,039,197 A | 4/1936 | Strieby |
| D121,570 S | 7/1940 | Hainsch |
| D141,336 S | 5/1945 | Yandell |
| 2,412,087 A | 12/1946 | Herbert |
| 2,443,997 A | 6/1948 | Town |
| D166,672 S | 5/1952 | Kantor |
| 2,645,222 A | 7/1953 | Capossela |
| D183,257 S | 7/1958 | Holder et al. |
| D187,882 S | 5/1960 | Wooten et al. |
| 3,334,356 A | 8/1967 | Abel |
| 4,228,548 A | 10/1980 | Cohen |
| D273,633 S | 5/1984 | Drum |
| D287,423 S | 12/1986 | Good et al. |
| D291,622 S | 9/1987 | Gray |
| D294,771 S | 3/1988 | Good et al. |
| 4,778,452 A | 10/1988 | Moden et al. |
| 4,781,200 A | 11/1988 | Baker |
| 5,033,864 A | 7/1991 | Lasecki et al. |
| D322,353 S | 12/1991 | Bennett |
| D331,830 S | 12/1992 | Unverferth |
| D344,175 S | 2/1994 | Decker |
| D344,402 S | 2/1994 | Hall |
| 5,299,120 A * | 3/1994 | Kaestle ................. A61B 5/7239 |
| | | | 600/479 |
| D345,854 S | 4/1994 | Fritz, Jr. |
| 5,385,537 A | 1/1995 | Davini |
| 5,505,199 A | 4/1996 | Kim |
| 5,515,865 A | 5/1996 | Scanlon |
| D375,195 S | 11/1996 | Panassidi |
| D378,949 S | 4/1997 | Lindaman |
| 5,623,734 A | 4/1997 | Pugliatti |
| D392,795 S | 3/1998 | Ogden |
| D397,797 S | 9/1998 | Chiang |
| D397,863 S | 9/1998 | Van De Steeg |
| 5,830,137 A | 11/1998 | Scharf |
| 5,842,982 A * | 12/1998 | Mannheimer ........ A61B 5/6829 |
| | | | 600/340 |
| 5,954,663 A | 9/1999 | Gat |
| 6,011,477 A | 1/2000 | Teodorescu et al. |
| 6,047,201 A | 4/2000 | Jackson, III |
| 6,102,856 A | 8/2000 | Groff et al. |
| 6,208,897 B1 | 3/2001 | Jorgenson et al. |
| 6,289,238 B1 | 9/2001 | Besson et al. |
| 6,454,708 B1 | 9/2002 | Ferguson et al. |
| 6,470,199 B1 | 10/2002 | Kopotic et al. |
| 6,492,634 B2 | 12/2002 | Marchitto et al. |
| 6,498,652 B1 | 12/2002 | Varshneya et al. |
| 6,553,242 B1 | 4/2003 | Sarussi |
| 6,553,256 B1 | 4/2003 | Jorgenson et al. |
| 6,569,095 B2 | 5/2003 | Eggers |
| D482,792 S | 11/2003 | McCormick et al. |
| 6,879,850 B2 | 4/2005 | Kimball |
| D516,025 S | 2/2006 | Quinn |
| 7,006,855 B1 | 2/2006 | Sarussi |
| 7,035,432 B2 | 4/2006 | Szuba |
| 7,171,251 B2 | 1/2007 | Sarussi et al. |
| D541,684 S | 5/2007 | Sandy et al. |
| 7,215,991 B2 | 5/2007 | Besson et al. |
| D553,251 S | 10/2007 | Watts |
| 7,359,741 B2 | 4/2008 | Sarussi |
| D569,985 S | 5/2008 | Ganapathy et al. |
| D585,605 S | 1/2009 | Kamradt |
| 7,590,438 B2 | 9/2009 | Sarussi et al. |
| 7,603,152 B2 | 10/2009 | Sarussi et al. |
| 7,606,607 B2 | 10/2009 | Sarussi et al. |
| D604,856 S | 11/2009 | Arbesman et al. |
| 7,613,490 B2 | 11/2009 | Sarussi et al. |

| | | | |
|---|---|---|---|
| 7,650,176 B2 | 1/2010 | Sarussi et al. |
| 7,713,223 B2 | 5/2010 | Weber et al. |
| 7,887,492 B1 | 2/2011 | Rulkov et al. |
| 7,937,128 B2 | 5/2011 | Al-Ali |
| 7,937,130 B2 | 5/2011 | Diab et al. |
| D649,718 S | 11/2011 | Baum et al. |
| 8,094,013 B1 | 1/2012 | Lee et al. |
| D665,539 S | 8/2012 | Manalo et al. |
| 8,265,723 B1 | 9/2012 | Mchale et al. |
| 8,347,144 B2 | 1/2013 | Khalak et al. |
| 8,417,351 B2 | 4/2013 | Kilger |
| D681,831 S | 5/2013 | Samlaska |
| D686,738 S | 7/2013 | Tabron et al. |
| D693,353 S | 11/2013 | Shu et al. |
| 8,620,448 B1 | 12/2013 | Delia |
| D706,429 S | 6/2014 | Julian et al. |
| 8,781,847 B2 | 7/2014 | Simms et al. |
| 8,814,792 B2 | 8/2014 | Raptis et al. |
| 8,847,740 B2 | 9/2014 | Kiani et al. |
| D719,267 S | 12/2014 | Vaccarella |
| 8,922,788 B2 | 12/2014 | Addison et al. |
| D722,382 S | 2/2015 | Lee et al. |
| 8,965,471 B2 | 2/2015 | Lamego |
| 9,028,405 B2 | 5/2015 | Tran |
| D730,761 S | 6/2015 | Spaeth et al. |
| D738,514 S | 9/2015 | Tagami et al. |
| 9,195,799 B2 | 11/2015 | Sze et al. |
| D746,161 S | 12/2015 | Vardi |
| D751,212 S | 3/2016 | Moreland et al. |
| 9,314,159 B2 | 4/2016 | Lyon et al. |
| D762,331 S | 7/2016 | Dixon |
| D781,568 S | 3/2017 | Workman |
| 9,642,538 B2 | 5/2017 | Newberry |
| 9,662,053 B2 | 5/2017 | Richards et al. |
| 9,693,719 B2 | 7/2017 | Al-Ali et al. |
| 9,693,730 B2 | 7/2017 | Workman et al. |
| 9,730,640 B2 | 8/2017 | Diab et al. |
| D798,170 S | 9/2017 | Toth et al. |
| D812,501 S | 3/2018 | Kuh et al. |
| D815,289 S | 4/2018 | Evers et al. |
| 9,936,917 B2 | 4/2018 | Poeze et al. |
| D821,571 S | 6/2018 | Stonecipher et al. |
| D822,717 S | 7/2018 | Lim |
| D823,466 S | 7/2018 | Marogil |
| D826,396 S | 8/2018 | Stonecipher et al. |
| D827,144 S | 8/2018 | Oliveira et al. |
| D828,807 S | 9/2018 | Yohai-Giochais |
| 10,076,244 B2 | 9/2018 | Lien |
| D829,889 S | 10/2018 | Hwang et al. |
| D830,537 S | 10/2018 | Hwang et al. |
| D830,555 S | 10/2018 | Lin et al. |
| 10,085,697 B1 | 10/2018 | Evans |
| D836,472 S | 12/2018 | Zhiyuan |
| 10,149,616 B2 | 12/2018 | Al-Ali et al. |
| D838,372 S | 1/2019 | Goering et al. |
| D840,024 S | 2/2019 | Stonecipher et al. |
| D842,715 S | 3/2019 | Fleet |
| D842,996 S | 3/2019 | Frick et al. |
| 10,219,709 B2 | 3/2019 | Basu |
| D852,965 S | 7/2019 | Bahney et al. |
| D855,040 S | 7/2019 | Fu et al. |
| D855,191 S | 7/2019 | Hong et al. |
| D856,953 S | 8/2019 | Chen et al. |
| 10,406,345 B2 | 9/2019 | Silver et al. |
| 10,420,470 B2 | 9/2019 | Kwon et al. |
| D864,148 S | 10/2019 | Munger et al. |
| 10,499,837 B2 | 12/2019 | Workman et al. |
| D873,420 S | 1/2020 | Hinshon |
| 10,537,270 B2 | 1/2020 | Sarussi et al. |
| 10,542,894 B2 | 1/2020 | Zhao et al. |
| D874,399 S | 2/2020 | Lockenwitz |
| D877,344 S | 3/2020 | Munger |
| D877,482 S | 3/2020 | Bunn et al. |
| D877,892 S | 3/2020 | Stonecipher et al. |
| D878,550 S | 3/2020 | Stonecipher et al. |
| 10,575,779 B2 | 3/2020 | Poeze et al. |
| D881,388 S | 4/2020 | Ziemann et al. |
| 10,709,335 B2 | 7/2020 | Matsuoka et al. |
| 10,721,785 B2 | 7/2020 | Al-Ali |

(56) References Cited

U.S. PATENT DOCUMENTS

| | | | |
|---|---|---|---|
| D893,034 S | 8/2020 | Kase et al. | |
| 10,736,507 B2 | 8/2020 | Muhsin et al. | |
| D895,124 S | 9/2020 | Wielunski et al. | |
| 10,835,406 B2 | 11/2020 | Erwin et al. | |
| 10,918,341 B2 | 2/2021 | Al-Ali et al. | |
| D914,218 S | 3/2021 | Govari et al. | |
| 10,973,495 B2 | 4/2021 | Vardi et al. | |
| 10,987,484 B1 | 4/2021 | Konda et al. | |
| D919,103 S | 5/2021 | Macpherson et al. | |
| D919,821 S | 5/2021 | Fosler et al. | |
| D926,325 S | 7/2021 | Barry et al. | |
| D928,704 S | 8/2021 | Ebrahimi et al. | |
| 11,079,225 B2 | 8/2021 | Ong et al. | |
| 11,083,371 B1 | 8/2021 | Szabados et al. | |
| D934,191 S | 10/2021 | Lv et al. | |
| D937,811 S | 12/2021 | Lee | |
| D938,835 S | 12/2021 | Yang et al. | |
| D940,881 S | 1/2022 | Hadley et al. | |
| D946,766 S | 3/2022 | Bunn et al. | |
| RE49,079 E | 5/2022 | Workman et al. | |
| 11,331,016 B1* | 5/2022 | Mohammadi | A61B 5/7221 |
| D954,032 S | 6/2022 | Bunn et al. | |
| 11,446,466 B1 | 9/2022 | Shvartzman et al. | |
| 11,504,002 B2 | 11/2022 | Muhsin et al. | |
| 11,504,062 B2 | 11/2022 | Poeze et al. | |
| D977,740 S | 2/2023 | Wingate | |
| D1,005,369 S | 11/2023 | Rao et al. | |
| D1,026,805 S | 5/2024 | Pedersen et al. | |
| D1,028,878 S | 5/2024 | Law et al. | |
| D1,039,997 S | 8/2024 | Bunn et al. | |
| 12,144,648 B2 | 11/2024 | Bunn et al. | |
| D1,054,427 S | 12/2024 | Au | |
| 2002/0013538 A1 | 1/2002 | Teller | |
| 2002/0133067 A1 | 9/2002 | Jackson, III | |
| 2002/0161291 A1 | 10/2002 | Kianl et al. | |
| 2003/0163287 A1 | 8/2003 | Vock et al. | |
| 2003/0181799 A1 | 9/2003 | Lindekugel et al. | |
| 2003/0229276 A1 | 12/2003 | Sarussi et al. | |
| 2004/0034293 A1 | 2/2004 | Kimball | |
| 2004/0133081 A1 | 7/2004 | Teller et al. | |
| 2004/0249299 A1 | 12/2004 | Cobb | |
| 2005/0113655 A1 | 5/2005 | Hull | |
| 2005/0228244 A1 | 10/2005 | Banet | |
| 2006/0276714 A1 | 12/2006 | Holt et al. | |
| 2007/0073119 A1 | 3/2007 | Wobermin et al. | |
| 2007/0073129 A1 | 3/2007 | Shah et al. | |
| 2007/0244377 A1 | 10/2007 | Cozad et al. | |
| 2007/0273504 A1 | 11/2007 | Tran | |
| 2008/0200312 A1 | 8/2008 | Tagliabue | |
| 2008/0221426 A1* | 9/2008 | Baker | A61B 5/6843 |
| | | | 600/407 |
| 2008/0275349 A1 | 11/2008 | Halperin et al. | |
| 2009/0112769 A1 | 4/2009 | Dicks et al. | |
| 2009/0216556 A1 | 8/2009 | Martin et al. | |
| 2009/0247849 A1 | 10/2009 | Mccutcheon et al. | |
| 2010/0077534 A1 | 4/2010 | Gill | |
| 2010/0081901 A1 | 4/2010 | Buice et al. | |
| 2010/0210986 A1 | 8/2010 | Sanders et al. | |
| 2010/0217158 A1 | 8/2010 | Wolfe et al. | |
| 2010/0234706 A1 | 9/2010 | Gilland | |
| 2010/0241018 A1 | 9/2010 | Vogel | |
| 2010/0274104 A1 | 10/2010 | Khan | |
| 2010/0317938 A1 | 12/2010 | Kuhn et al. | |
| 2011/0288379 A1 | 11/2011 | Wu | |
| 2012/0083670 A1 | 4/2012 | Rotondo et al. | |
| 2012/0130210 A1 | 5/2012 | Kall | |
| 2012/0157757 A1 | 6/2012 | Ten et al. | |
| 2012/0179479 A1 | 7/2012 | Waterson et al. | |
| 2012/0209088 A1 | 8/2012 | Romem | |
| 2012/0226117 A1 | 9/2012 | Lamego et al. | |
| 2012/0232416 A1 | 9/2012 | Gilham et al. | |
| 2012/0245447 A1 | 9/2012 | Karan et al. | |
| 2012/0253142 A1 | 10/2012 | Meger et al. | |
| 2012/0299732 A1 | 11/2012 | Vogel | |
| 2013/0021154 A1 | 1/2013 | Solomon et al. | |
| 2013/0030259 A1 | 1/2013 | Thomsen et al. | |
| 2013/0072765 A1 | 3/2013 | Kahn et al. | |
| 2013/0090586 A1 | 4/2013 | Dennis | |
| 2013/0171599 A1 | 7/2013 | Bleich et al. | |
| 2013/0261415 A1 | 10/2013 | Ashe et al. | |
| 2013/0289361 A1 | 10/2013 | Bridge et al. | |
| 2014/0180023 A1 | 6/2014 | Stivoric et al. | |
| 2014/0275808 A1* | 9/2014 | Poeze | A61B 5/742 |
| | | | 600/300 |
| 2015/0157263 A1* | 6/2015 | Workman | A61B 5/6898 |
| | | | 600/595 |
| 2015/0164438 A1 | 6/2015 | Halperin et al. | |
| 2015/0201846 A1 | 7/2015 | Maiershon et al. | |
| 2015/0216454 A1 | 8/2015 | Kasahara et al. | |
| 2015/0250419 A1 | 9/2015 | Cooper et al. | |
| 2015/0342527 A1 | 12/2015 | Karnik et al. | |
| 2015/0374293 A1 | 12/2015 | Horito | |
| 2016/0058380 A1 | 3/2016 | Lee et al. | |
| 2016/0066827 A1 | 3/2016 | Workman et al. | |
| 2016/0120500 A1 | 5/2016 | Myklebust et al. | |
| 2016/0174898 A1 | 6/2016 | Udoh et al. | |
| 2016/0192856 A1 | 7/2016 | Lee | |
| 2017/0014040 A1 | 1/2017 | Shim et al. | |
| 2017/0209055 A1* | 7/2017 | Pantelopoulos | A61B 5/02438 |
| 2017/0239098 A1 | 8/2017 | Schettler | |
| 2017/0245791 A1 | 8/2017 | Workman et al. | |
| 2017/0296075 A1* | 10/2017 | Loseu | A61B 5/02416 |
| 2017/0315511 A1 | 11/2017 | Shim et al. | |
| 2018/0317785 A1 | 11/2018 | MacDonald et al. | |
| 2019/0008432 A1 | 1/2019 | Bashan et al. | |
| 2019/0028662 A1 | 1/2019 | Kulcke et al. | |
| 2019/0150527 A1 | 5/2019 | Oleson et al. | |
| 2019/0209060 A1 | 7/2019 | Katra | |
| 2019/0223806 A1 | 7/2019 | Bennet et al. | |
| 2019/0298175 A1 | 10/2019 | Matsui et al. | |
| 2020/0015690 A1 | 1/2020 | Choi et al. | |
| 2020/0044466 A1 | 2/2020 | Piercey et al. | |
| 2020/0060590 A1 | 2/2020 | Workman et al. | |
| 2020/0253474 A1 | 8/2020 | Muhsin et al. | |
| 2020/0289014 A1 | 9/2020 | Park et al. | |
| 2021/0161442 A1 | 6/2021 | Welch et al. | |
| 2021/0193977 A1 | 6/2021 | Reykhert | |
| 2021/0393200 A1 | 12/2021 | Bunn et al. | |
| 2022/0218291 A1 | 7/2022 | Al-Ali et al. | |
| 2022/0248984 A1 | 8/2022 | Poeze et al. | |
| 2023/0157543 A1 | 5/2023 | Muhsin et al. | |
| 2023/0165530 A1 | 6/2023 | Poeze et al. | |
| 2023/0284943 A1 | 9/2023 | Scruggs et al. | |
| 2023/0301562 A1 | 9/2023 | Scruggs et al. | |
| 2025/0032047 A1 | 1/2025 | Bunn et al. | |
| 2025/0241589 A1 | 7/2025 | Bunn et al. | |
| 2026/0069211 A1 | 3/2026 | Bunn et al. | |

FOREIGN PATENT DOCUMENTS

| | | |
|---|---|---|
| CN | 201480129 U | 5/2010 |
| CN | 204245285 U | 4/2015 |
| CN | 204292312 U | 4/2015 |
| CN | 303928185 | 11/2016 |
| EP | 1139865 A1 | 10/2001 |
| EP | 2818062 A1 | 12/2014 |
| IL | 121079 | 1/2005 |
| JP | 01-189604 A | 7/1989 |
| JP | 11-089604 A | 4/1999 |
| JP | 2008-194323 | 8/2008 |
| WO | WO 9004352 A1 | 5/1990 |
| WO | 00/28888 A1 | 5/2000 |
| WO | 02/85200 A2 | 10/2002 |
| WO | 2004/075746 A2 | 9/2004 |
| WO | 2004/075750 A1 | 9/2004 |
| WO | 2008/123903 A1 | 10/2008 |
| WO | 2008/135985 A1 | 11/2008 |
| WO | 2009/049104 A1 | 4/2009 |
| WO | 2011/039745 A1 | 4/2011 |
| WO | 2012/025829 A2 | 3/2012 |
| WO | 2012/082297 A2 | 6/2012 |
| WO | 2014/035836 A1 | 3/2014 |
| WO | 2014/162135 A1 | 10/2014 |
| WO | 2015/005796 A1 | 1/2015 |

(56)                    References Cited

FOREIGN PATENT DOCUMENTS

| WO | WO 2016178986 A1 | 11/2016 |
| WO | WO 2019175122 A2 | 9/2019 |
| WO | WO 2019181268 A1 | 9/2019 |
| WO | WO 2019214990 A1 | 11/2019 |
| WO | WO 2019226692 A1 | 11/2019 |
| WO | 2021/262552 A1 | 12/2021 |

OTHER PUBLICATIONS

Ohmeda Biox 3700 Pulse Oximeter Operating/Maintenance Manual, 1118-301, Jun. 1, 1988 (Year: 1988).*

P.D. Davis et al., "Basic Physics and Measurement in Anaesthesia (Fourth Edition)," 1995, Chapter 18—Oxygen Measurement, pp. 235-249, excerpt only, excerpt accessed via sciencedirect.com, "Pulse Oximeter," https://www.sciencedirect.com/topics/engineering/pulse-oximeter, accessed Sep. 5, 2025 (Year: 1995).*

Alharbi et al.; "Oxygen Saturation Measurements from Green and Orange Illuminations of Multi-Wavelength Optoelectronic Patch Sensors;" Sensors (Basel); (Jan. 2019); 17 pages; vol. 19, No. 1; <doi: 10.3390/s19010118 >.

BSX Technologies; "Red Light Versus Green Light: The Future of Optical Sensing in Wearable Devices;" (Aug. 16, 2016); 5 pages; (Retrieved on Feb. 20, 2022); retrieved from <URL: https://medium.com/bsxtechnologies/red-light-versus-green-light-74fdd5fe7027 >.

Castaneda et al.; "A Review on Wearable Photoplethysmography Sensors and their Potential Future Applications in Health Care;" International Journal of Biosensors & Bioelectronics; (2018); pp. 195-202; vol. 4, No. 4; <doi: 10.15406/ijbsbe.2018.04.00125 >.

Chang et al.; "MW-PPG Sensor: An on-Chip Spectrometer Approach;" Sensors (Basel); (Sep. 2019); pp. 3698; vol. 19, No. 17; <doi: 10.3390/s19173698 >.

EDN; "LED-based Sensors for Wearable Fitness Tracking Products;" edn.com; (Dec. 16, 2014); 8 pages; Retrieved from <URL: edn.com/led-based-sensors-for-wearable-fitness-tracking-products/ >.

Cardiac Insight Raises $4.5M, wins FDA Approval to Launch Wearable ECG Sensor, publication date Apr. 20, 2017, (online) URL: https ://www.geekwire.com/2017 /cardiac-insight-raises-2-m-launches-wearable-ecg-sensor/ (Year: 2017).

Communication under Rule 71(3) EPC received for European Patent Application No. 13832064.3, mailed on Apr. 1, 2021, 6 pages.

Crook "Owlet Infant Health Tracker Takes the Wearable Revolution into the Crib" Techcrunch, Owlet article published Jan. 8, 2014.

Decision to grant a European patent pursuant to Article 97(1) EPC received for European Patent Application No. 13832064.3, mailed on Jul. 15, 2021, 2 pages.

Ex Parte Quayle Action received for U.S. Appl. No. 29/826,925, mailed on Jun. 6, 2024, 6 pages.

Final Office Action received for U.S. Appl. No. 16/673,041, mailed on Apr. 28, 2023, 13 pages.

Final Office Action received for U.S. Appl. No. 16/673,041, mailed on Jun. 28, 2022, 15 pages.

Final Office Action received for U.S. Appl. No. 29/592,388, mailed on Feb. 15, 2019.

First Office Action received for Chinese Patent Application No. 201810952168, mailed on Nov. 2, 2020, 12 pages.

Help Me Find a Dream Sock Sensor for the Owlet Smart Sock, Reddit r/HelpMeFind, publication date Jan. 10, 2022, (online) URL: https://www.reddit.com/r/HelpMeFind/comments/sOnt94/help_me_find_a_dream_sock_sensor_for_the_owlet/ (Year: 2022).

International Preliminary Report on Patentability issued in PCT/US2013/056511 mailed Mar. 12, 2015.

International Search Report and Written Opinion issued in PCT/US2013/056511 mailed Dec. 10, 2013.

Masimo Stork—A Revolutionary Baby Monitor; https://www.masimostork.com/en-us/ retrieved on Jan. 11, 2024.

Non-Final Office Action received for U.S. Appl. No. 16/503,335, mailed on Jul. 28, 2021, 15 pages.

Non-Final Office Action received for U.S. Appl. No. 16/673,041, mailed on Feb. 22, 2022, 16 pages.

Notice of Allowance issued in U.S. Appl. No. 29/504,663 dated Jan. 4, 2017.

Notice of Allowance received for U.S. Appl. No. 15/594,240, mailed on Aug. 7, 2019.

Notice of Allowance received for U.S. Appl. No. 16/503,335, mailed on Jan. 13, 2022, 9 pages.

Notice of Allowance received for U.S. Appl. No. 16/503,335, mailed on Mar. 31, 2022, 2 pages.

Notice of Allowance received for U.S. Appl. No. 29/738,984, mailed on Apr. 16, 2024, 7 pages.

Notice of Allowance received for U.S. Appl. No. 29/826,925, mailed on Aug. 8, 2024, 5 pages.

Office Action issued in U.S. Appl. No. 29/504,663 dated Sep. 8, 2016.

Office Action received for BR Application No. 112015003844, mailed on Jun. 18, 2020, 4 pages.

Office Action received for Chinese Application No. 201810952168, mailed on Aug. 17, 2021, 19 pages (4 pages of English Translation and 5 pages of Original Document).

Office Action received for Chinese Application No. 201810952168, mailed on May 13, 2021, 19 pages (9 pages of English Translation and 10 pages of Original Document).

Office Action received for U.S. Appl. No. 15/594,240, mailed on Apr. 29, 2019.

Office Action received for U.S. Appl. No. 29/592,388, mailed on Jul. 26, 2018.

Owlet Instagram page, [online], [site visited Aug. 3, 2016]. Oldest photo of invention posted on Jun. 6, 2014, <URL: https ://www.instagram.com/owletcare/?hl=en>.

Owlet Protection Enterprises, LLC. (applicant), [online], [site visited Aug. 3, 2016]. Available from Internet, <URL: http://www.owletcare.com/>.

Owlet Smart Sock 2—The Future of Parenting, posted at youtube.com, posted Mar. 29, 2017, online, URL: https://www.youtube.com/watch?v=GFk2HxIOmzk (Year: 2017).

Owlet Stops Selling Sleep Sock After Receiving Warning from the FDA, publication date Dec. 2, 2021, (online) URL: https://www.whsv.com/2021 /12/02/owlet-stops-selling-sleep-sock-after-receiving-warning-fda/#: - :text= The % 20comany%20plans%20to%20offer, U.S. %20sometime%20in%20January%202022. (Year: 2021).

Owlet Twitter page, [online], [site visited Aug. 3, 2016]. Oldest photo of invention posted on May 7, 2015 (different prototype photo posted on Jan. 8, 2014), <URL: https ://twitter.com/owletbabycare?ref_src=twsrc%5Egoogle%7Ctwcamp%5Eserp%7Ctwgr%5Eauthor>.

Supplementary European Search Report, EP 13832064 dated May 3, 2016.

Techcrunch, Owlet article published Jan. 8, 2014, [online], [site visited Aug. 3, 2016]. <URL: https://techcrunch.com/2014/01/08/owlet-infant-health-tracker-takes-the-wearable-revolution-into-the-crib/>.

U.S. Application filed on Jan. 30, 2017, by Bunn., U.S. Appl. No. 29/592,388.

Notice of Allowance received for U.S. Appl. No. 19/180,866, mailed on Aug. 14, 2025, 9 pages.

International Preliminary Report on Patentability received for PCT Patent Application No. PCT/US21/38115, mailed on Jan. 5, 2023, 08 pages.

International Preliminary Report on Patentability received for PCT Patent Application No. PCT/US21/38121, mailed on Jan. 5, 2023, 09 pages.

International Search Report and Written Opinion received for PCT Patent Application No. PCT/US21/38115, mailed on Oct. 15, 2021, 09 pages.

International Search Report and Written Opinion received for PCT Patent Application No. PCT/US21/38121, mailed on Oct. 13, 2021, 12 pages.

Jordan Crook, Owlet Infant Health Tracker Takes The Wearable Revolution Into The Crib, https://techcrunch.com/2014/01/08/owlet-infant-health-tracker-takes-the-wearable-revolution-into-the-crib/, Jan. 8, 2014, viewed on Oct. 6, 2023.

(56)          References Cited

OTHER PUBLICATIONS

Notice of Allowance received for U.S. Appl. No. 14/001,503, mailed on Apr. 14, 2017.
Notice of Allowance received for U.S. Appl. No. 17/352,081, mailed on Jul. 11, 2024, 7 pages.
Notice of Allowance received for U.S. Appl. No. 29/504,663, mailed on Jan. 4, 2017.
Office Action received for U.S. Appl. No. 14/001,503, mailed on Apr. 19, 2016.
Office Action received for U.S. Appl. No. 14/001,503, mailed on Aug. 21, 2015.
Office Action received for U.S. Appl. No. 14/001,503, mailed on Oct. 20, 2016.
Office Action received for U.S. Appl. No. 29/504,663, mailed on Sep. 8, 2016.
Office Action received for UK Patent Application No. 2300320.5, mailed on Aug. 30, 2024, 3 pages.
Office Action received for UK Patent Application No. 2300320.5, mailed on May 7, 2024, 2 pages.
Requirement for Restriction/Election received for U.S. Appl. No. 19/180,866, mailed on Jun. 18, 2025, 6 pages.
Shamsir et al., "Smart infant-monitoring system with machine learning model to detect physiological activities and ambient conditions," IEEE International Instrumentation and Measurement Technology Conference (I2MTC). IEEE, 2020, pp. 6.
Office Action received for Mexican Patent Application No. MX/a/2023/000098, mailed on Sep. 4, 2025, 5 pages.
Notice of Allowance received for U.S. Appl. No. 19/180,866, mailed on Sep. 2, 2025, 5 pages.
Notice of Allowance received for U.S. Appl. No. 19/180,866, mailed on Sep. 30, 2025, 2 pages.
Office Action received for Mexican Patent Application No. MX/a/2023/000098, mailed on Mar. 9, 2026, 32 pages (16 pages of English Translation and 16 pages of Original Document).

* cited by examiner

100

201

202

226

227

200

250

MONITORING DEVICE

PRIORITY CLAIM

This application claims priority to U.S. Ser. No. 63/042,511 filed on Jun. 22, 2020 entitled "Monitoring Device" which is incorporated herein by reference in its entirety. This application also claims priority to U.S. Ser. No. 63/042,203 entitled "Infant Monitoring Device" which was filed on Jun. 22, 2020 and is incorporated herein by reference in its entirety.

FIELD OF THE DISCLOSURE

Disclosure embodiments relate generally to monitoring devices, and more particularly to a wearable garment for collecting and analyzing personal data and specifically for methods, devices, and systems for determining proper placement of a monitoring device on a portion of the body of a subject.

BACKGROUND

For many years, problems associated with Sudden Infant Death Syndrome (SIDS) have been addressed by the health community. SIDS is considered a significant cause of infant mortality during the first year of life. In many cases, SIDS is designated as the cause of death whenever a healthy infant dies suddenly during sleep for no apparent reason; though the cause of SIDS is allusive. Because infant survival can be improved if the onset of SIDS is detected, efforts have been expended in developing systems for monitoring an infant's heart rate, blood oxygen, or breathing rate during sleep. Systems for non-medical use have been developed, but have proven to be incapable of providing consistent, uniform, comfortable, and dependable monitoring of a child without suffering from false alarm signals. Therefore, it is one object of the present technology to provide a consistent, comfortable, and dependable health monitoring system which is employed for monitoring the overall health of an infant and producing an alarm signal whenever preset criteria are not met. Other and more specific objects will be described hereinafter.

SUMMARY

Aspects of the technology are directed towards a wireless monitoring sensor for monitoring the biological parameters of an infant or other subject. Aspects of the technology include a sensing module (or wearable monitor) that is removably disposed about a wearable garment. The sensing module comprises a plurality of sensor assemblies that are disposed about the sensing module such that when the sensing module placed about the subject, the sensor assemblies can collect data with respect to the subject, including biological data. The sensor assemblies are optimized to determine when the sensing module is properly placed about the subject to minimize inaccurate readings.

BRIEF DESCRIPTION OF THE DRAWINGS

Embodiments will become more fully apparent from the following description, taken in conjunction with the accompanying drawings. It is to be understood that these drawings merely depict exemplary embodiments and are not to be considered limiting of the disclosure's scope. It will be readily appreciated that the components of the embodiments, as generally described and illustrated in the figures herein, could be arranged and designed in a wide variety of different configurations. Nonetheless, the technology will be described and explained with additional specificity and detail through the use of the accompanying drawings in which.

DESCRIPTION OF ASPECTS OF THE TECHNOLOGY

Figures 1A, 1B:
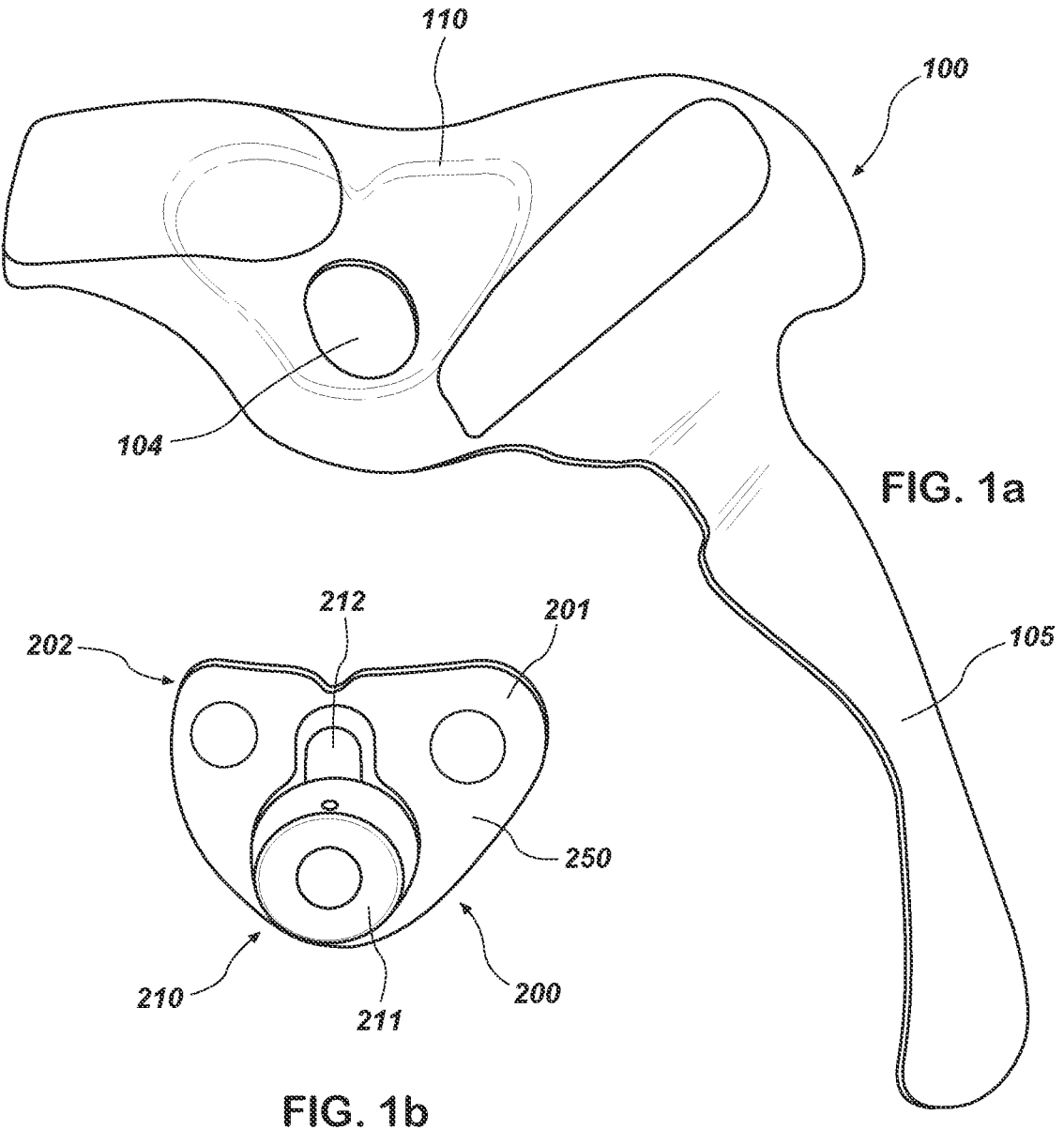
FIG. 1a is a perspective front view of a garment in accordance with one aspect of the technology.
FIG. 1b is a perspective front view of a sensor module in accordance with one aspect of the technology.
Figures 2A, 2B:
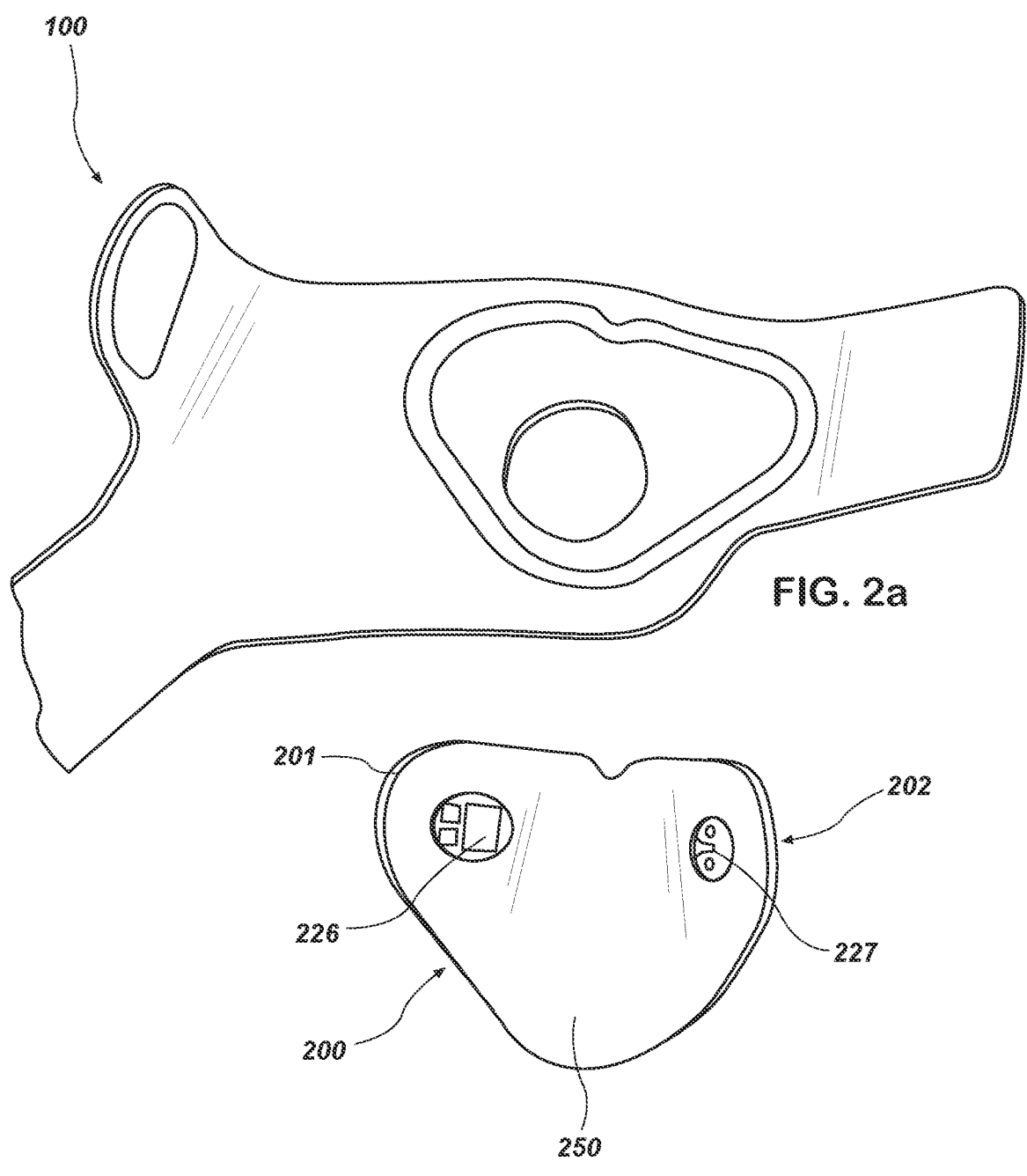
FIG. 2a is a perspective back view of a garment in accordance with one aspect of the technology.
FIG. 2b is a perspective back view of a sensor module in accordance with one aspect of the technology.
Figure 3:
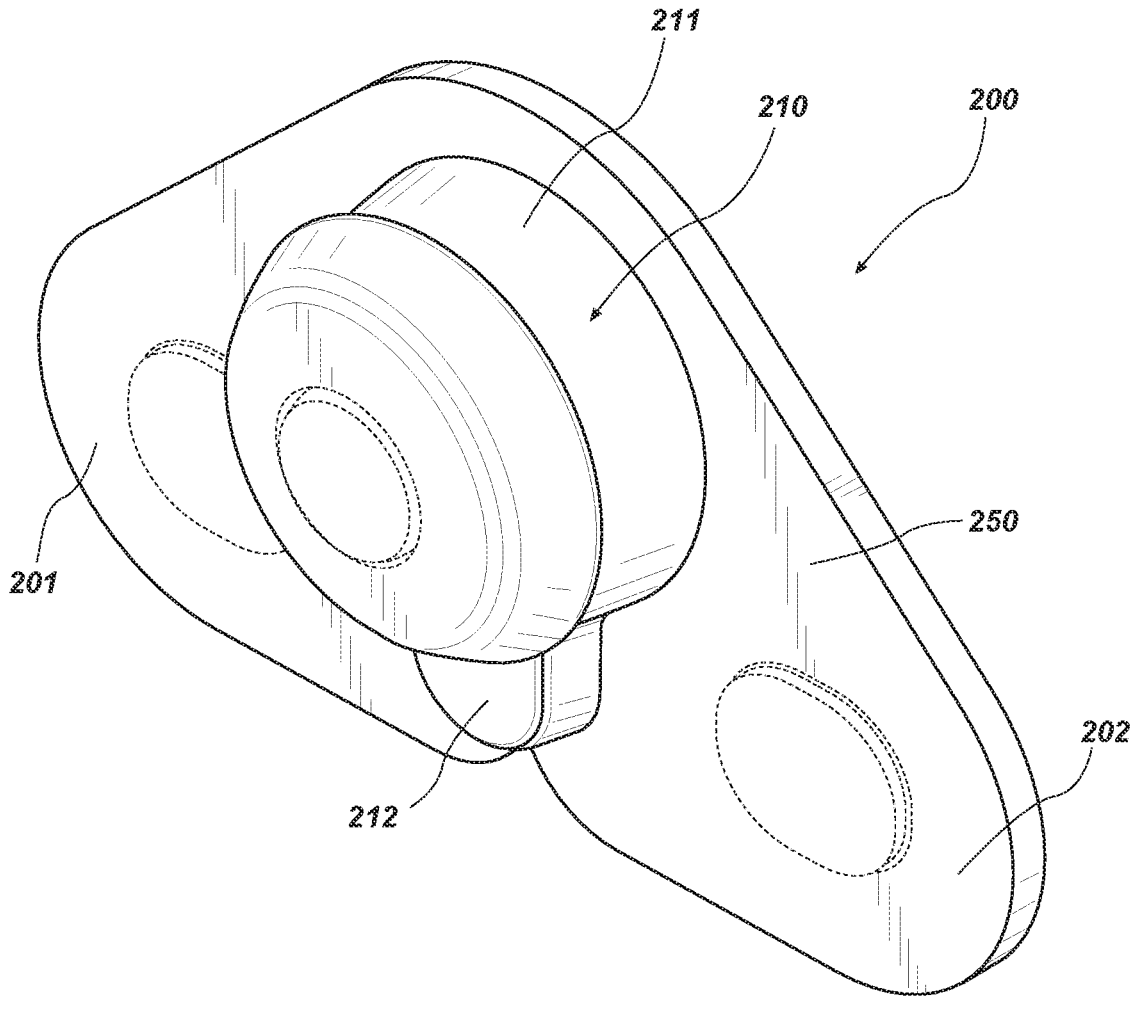
FIG. 3 is a perspective side view of a sensor module in accordance with one aspect of the technology.
Figure 4:
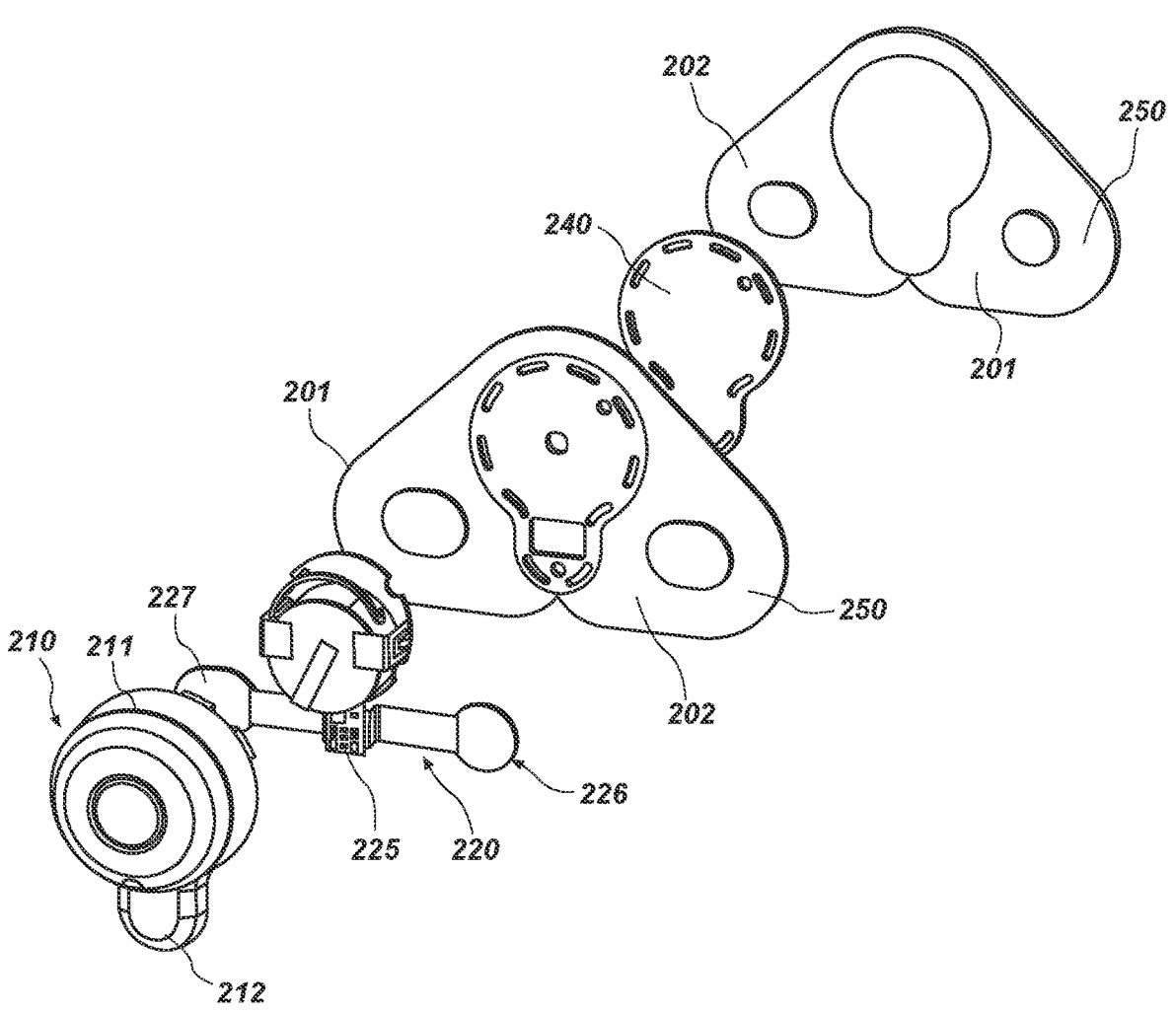
FIG. 4 is an exploded view of a sensor module in accordance with one aspect of the technology.
Figures 5A, 5B:
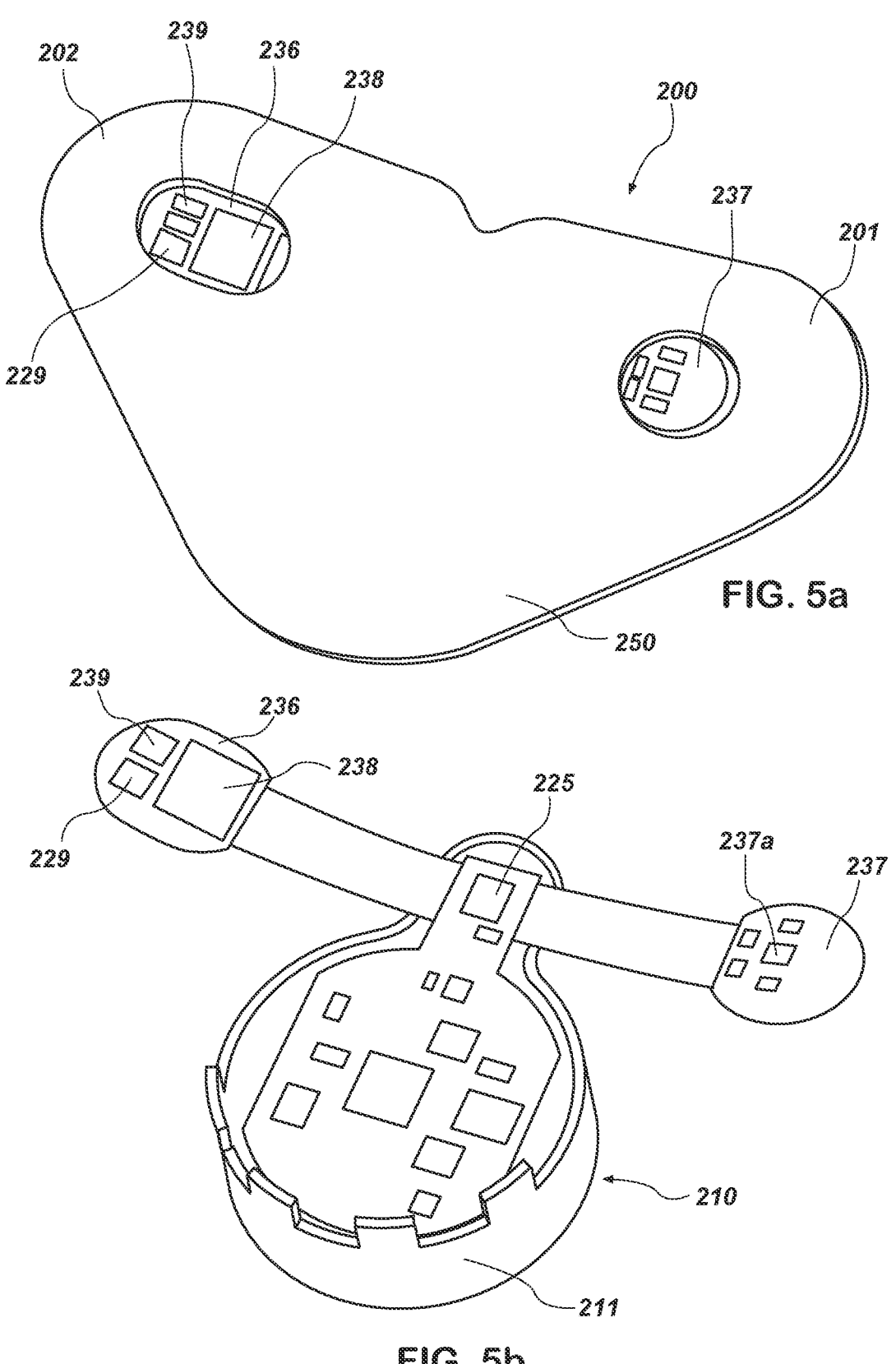
FIG. 5a is a back perspective view of a sensor module in accordance with one aspect of the technology.
FIG. 5b is a back perspective view of a portion of a sensor module in accordance with one aspect of the technology.

The following detailed description includes reference to the accompanying drawings, which form a part hereof and in which are shown, by way of illustration, exemplary embodiments. It is believed that proper placement of wearable monitors will improve the performance of the monitor. However, before the present technology is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations. Unless defined otherwise, all technical and scientific terms used herein have the same meaning as commonly understood by one of ordinary skill in the art to which this disclosure belongs.

As used in this specification, the singular forms "a," "an" and "the" include plural referents unless the context clearly dictates otherwise. Thus, for example, reference to "a line" includes a plurality of such lines.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this specification it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in a fluidic or non-fluidic manner.

Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms."

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.8, 3, 3.1, 4, 4.6, and 5, individually.

This same principle applies to ranges reciting only one numerical value as a minimum or a maximum. Furthermore, such an interpretation should apply regardless of the breadth of the range or the characteristics being described.

As used herein, "enhanced," "improved," "performance-enhanced," "upgraded," "improvement," and the like, when used in connection with the description of a device, component, or process, refers to a characteristic of the device, component or process that provides measurably better form, function, or outcome as compared to previously known devices or processes. This applies both to the form and function of individual components in a device or process, as well as to such devices or processes as a whole.

Reference throughout this specification to "an example" means that a particular feature, structure, or characteristic described in connection with the example is included in at least one embodiment. Thus, appearances of the phrase "in an example" in various places throughout this specification are not necessarily all referring to the same embodiment.

Example Embodiments

It should be understood that the aspects of the technology discussed herein are contemplated for use with a wearable monitor. For purposes of illustrating the various aspects of the methods and systems claimed herein, the discussion below will be primarily directed to describing exemplary embodiments directed to methods, systems, and devices used to determine if an infant monitoring device is properly disposed about the body of the infant in order to obtain optimal measurements of the infant. It should be noted, however, that the elements and principles discussed herein are applicable to other applications, including, but without limitation, optimizing placement of a wearable monitor on any body part of a subject. It is also noted that discussion of methods and systems herein can be interchangeable with respect to specific aspects. In other words, specific discussion of one apparatus, method, or system (or components thereof) herein is equally applicable to other aspects as they relate to the system, apparatus, or methods, and vice versa.

An initial overview of technology embodiments is provided below and specific technology embodiments are then described in further detail. This initial summary is intended to aid readers in understanding the technology more quickly, but is not intended to identify key or essential technological features, nor is it intended to limit the scope of the subject matter.

In particular, aspects of the technology are directed towards a wireless monitoring sensor for monitoring the biological parameters of an infant or other subject. Aspects of the technology include a sensing module (or wearable monitor) 200 that is removably disposed about a sock or garment 100 or foot-band adapted to be placed about the foot of an infant, though in other applications the wearable monitor could be placed on other portions of the subject in other arrangements. The sensing module 200 comprises a plurality of sensor assemblies 236, 237 that are disposed on opposing sides of the sensing module 200 such that when the sensing module 200 is placed about the foot (or other body part) of the infant, the sensor assemblies 236, 237 can collect data with respect to the infant (or other subject), including biological data. The sensor assemblies 236, 237 are configured to determine when the sensing module 200 is properly placed on the foot of the infant to minimize inaccurate readings. While placement of the different sensor assemblies 236, 237 on opposing sides of the foot (or other body part) is shown in different aspects of the technology, it is understood that the LEDs 237a and photodiode 238 can be placed on a single sensor assembly and placed on one side of the body, measuring reflectivity of light from the tissue rather than absorption. In one aspect of the technology, the fabric of the sock or garment 100 may be a stretchable fabric, for example a woven elastomer in the class of segmented co-polyesters such as polyester-polyurethane copolymer fibers alone or blended with cotton or other natural fibers or synthetic polymer fibers such as polyester, nylon, acrylic, and the like. For example, in one aspect of the technology, the fabric of the garment comprises a nylon, polyester, spandex blend. The fabric is configured to wrap around the foot (or other body part) of an infant (or other subject) and couple to itself using hook and loop fasteners, snaps, zippers, belts, velcro, or other fasteners known in the art.

With reference generally to FIGS. 1-6, the sock or garment 100 comprises a generally planar material having a first portion 105 configured to wrap around the foot of an infant and a second portion 110 extending above and away from the first portion the second portion being configured to wrap around the leg and/or ankle of the infant. The sock or garment 100 is configured to receive a removable sensor module 200 thereon and hold the sensor module 200 in an optimal position about the foot of the infant to take measurements of the infant. In one aspect of the technology, the sensor module 200 comprises a contact charging enclosure 210 which houses an electronics sub-assembly 220. The sensor module 200 further comprises an attachment plate 240 and a fabric enclosure 250. In one aspect, a top portion 211 and bottom portion 212 of the charging enclosure 210 are disposed through an aperture of the fabric enclosure 250. The top portion 211 of the charging enclosure 210 is configured to be disposed through an aperture 104 within the sock or garment 100.

In one aspect of the technology, the sensor module 200 and the attendant electronics sub-assembly 220 comprises a microcontroller (processor) coupled with one or more sensors, including sensor assemblies 236, 237. The sensor module 200 may be powered by a rechargeable battery (or other power source) within the sub-assembly 220. Data storage may be provided to store computer software executable by the microcontroller and the received sensor data from the one or more sensors. The sensor module 200 may further include a wireless interface for interfacing with other devices (e.g., smart phone, computer, etc.). The sensor module 200 may further include an audio/visual/tactile feedback device for outputting signals to a user. LED status indicators may also be provided.

In one aspect of the technology, the microcontroller (which may be part of PCB 225) may be configured to receive and process the sensor data from the one or more sensors. In certain aspects, the microcontroller is configured to monitor user activity to identify different biological data of the subject. Optionally, the microcontroller may be configured to transmit the sensor data from the one or more sensors to a processor housed separately from the microcontroller (e.g., a base station, remote server, cloud storage, etc.) for data analysis at a separate processor. This may be beneficial when increased processing power is desired and/or when reducing a footprint of sensor module 200. The separate processor may be a portable electronic device (e.g., PDA, smartphone, tablet computer, watch, or the like) of the user, a desktop computer (a personal computer of the user, a clinician's computer), etc.

The one or more sensors may include accelerometers, gyroscopes, magnetometers, infrared/temperature sensors, heat flux sensors, pressure sensors, photodiodes, LED/photodiode pairs and/or combinations thereof. In some embodiments, the one or more sensors may be 3-axis sensors (e.g., 3-axis gyroscopes, 3-axis accelerometers, 3-axis magnetometers, etc.). Optionally, the one or more sensors may comprise a plurality of single axis sensors (e.g., one or more of: x-axis gyroscopes, y-axis gyroscopes, z-axis gyroscopes, x-axis accelerometer, y-axis accelerometer, z-axis accelerometer, x-axis magnetometers, y-axis magnetometers, z-axis magnetometers, etc.). For example, in some aspects, the sensor module 200 may feature a user-programmable gyroscope full-scale range of ±250, ±500, ±1000, and ±2000°/sec (dps). In some embodiments, sensor module 200 may feature a user-programmable accelerometer full-scale range of ±2 g, ±4 g, ±8 g, and ±16 g. In some aspects, the sensor module may feature a magnetometer full-scale range of ±4800 µT. The sensor module 200 may further include analog-to-digital converters for digitizing the output from the one or more sensors for data recording and analysis. In some aspects, the one or more sensors may provide force data (e.g., Fx, Fy, Fz) and/or orientation data (e.g., a recline angle θ, a side tilt angle φ) to the microcontroller for processing. The rechargeable battery may be a Li-ion battery for example. The battery may be recharged via a Universal Serial Bus (USB) port, mini-USB port, micro-USB port, wireless inductive charging, or the like. Wireless interface may provide wireless connection to smartphones, tablets, or other mobile devices. For example, in some embodiments, data may be stored on the sensor module 200 and transmitted for processing at a later time. Alternatively, the sensor module 200 may transmit the data in substantial real-time to a user's personal device for data processing. In some aspects, the wireless interface comprises a Wi-Fi or Bluetooth wireless interface.

In one aspect of the technology, a sensor module 200 is configured to couple to the sock or garment 100 such that when the sock or garment 100 is properly placed on the foot of the infant, data with respect to the infant (e.g., temperature, heart-rate, blood oxygen, etc.) may be obtained. The general shape of the sensor module 200, when positioned on the sock or garment 100, advantageously positions the sensors about an exterior portion of the infant's foot for optimal measurement of important biological data. For example, the sensor module 200 comprises opposing wings 201, 202 that houses sensor assemblies 236, 237 configured to propagate light onto the skin of the infant as well as through the skin of the infant. In some aspects of the technology, the sensor module 200 is configured to detect the amount of light absorbed by the skin. However, in other aspects of the technology, the sensor module 200 is configured to measure the amount of light reflected from the skin of the subject.

In one aspect of the technology, the sensors use pulse-oximetry information to compute heart rate and/or oxygen levels. Generally speaking, information is gathered by propagating a wavelength of light onto tissue and recording the measurements of the resulting signal. As noted herein, in some instances, the amount of light reflected off the tissue is measured and/or recorded. In other instances, the amount of light absorbed by the tissue is measured and/or recorded. When the sensor module 200 is not properly placed on the foot of the infant, ambient light can produce noise signals that cause errant measurements of heart rate, oxygen, or both. These errant measurements are undesirable.

In addition, improper positioning of the sensor module 200 about the subject can result in certain wavelengths of light (e.g., infrared wavelengths) used to measure one data point (e.g., proximity of the sensor to the target) that may not be coordinated with the timing of light transmission used for pulse-oximetry. For example, if an infrared proximity sensor is being used to measure the proximity of the device to a target, the timing of the infrared proximity light propagation may not be properly synchronized with the light propagation used to measure pulse-oximetry. This may result in errant infrared (or other) wavelengths of light being propagated during a pulse-oximetry light transmission event. Moreover, ambient light may "leak" onto a photodiode, or other pulse-oximetry measurement sensor, if the device is not properly positioned. In both instances, this can result in poor or inaccurate pulse-oximetry readings.

In one aspect of the technology, two or more specific wavelengths of light that have distinctly different optical characteristics (e.g. optical loss, transmissivity, absorption rates, etc.) when propagated onto a medium of interest (e.g. foot, arm, hand, neck, etc.) are used to help determine proper placement of the measurement device. These wavelengths of light are propagated onto the medium of interest substantially sequentially and the resulting reflection and/or absorption of the light is measured. In one aspect of the technology, the time between transmission of the first and second wavelengths is between 40 and 60 microseconds, though different time intervals and sequences of light propagation are contemplated herein. For example, in another aspect, red light (650 nm to 670 nm) is propagated for 55 microseconds after which no light is propagated for a period of 55 microseconds. Infrared light (930 nm to 950 nm) for a period of 55 microseconds substantially immediately after which blue light (450 nm to 470 nm) for 55 microseconds. After the blue light is propagated, no light is propagated for a period ranging from 5 to 7 milliseconds after which the light propagation cycle begins again. In each cycle, the characteristics of the received light (e.g. the optical loss) for each wavelength used are compared to determine if the sensor module 200 is properly placed and also to measure and collect pulse-oximetry data from the target. In aspects of the technology, the results of a repeated comparison is used to provide a confidence interval with respect to the accuracy of the measurements being computed by the wearable sensor.

Figures 6A, 6B:
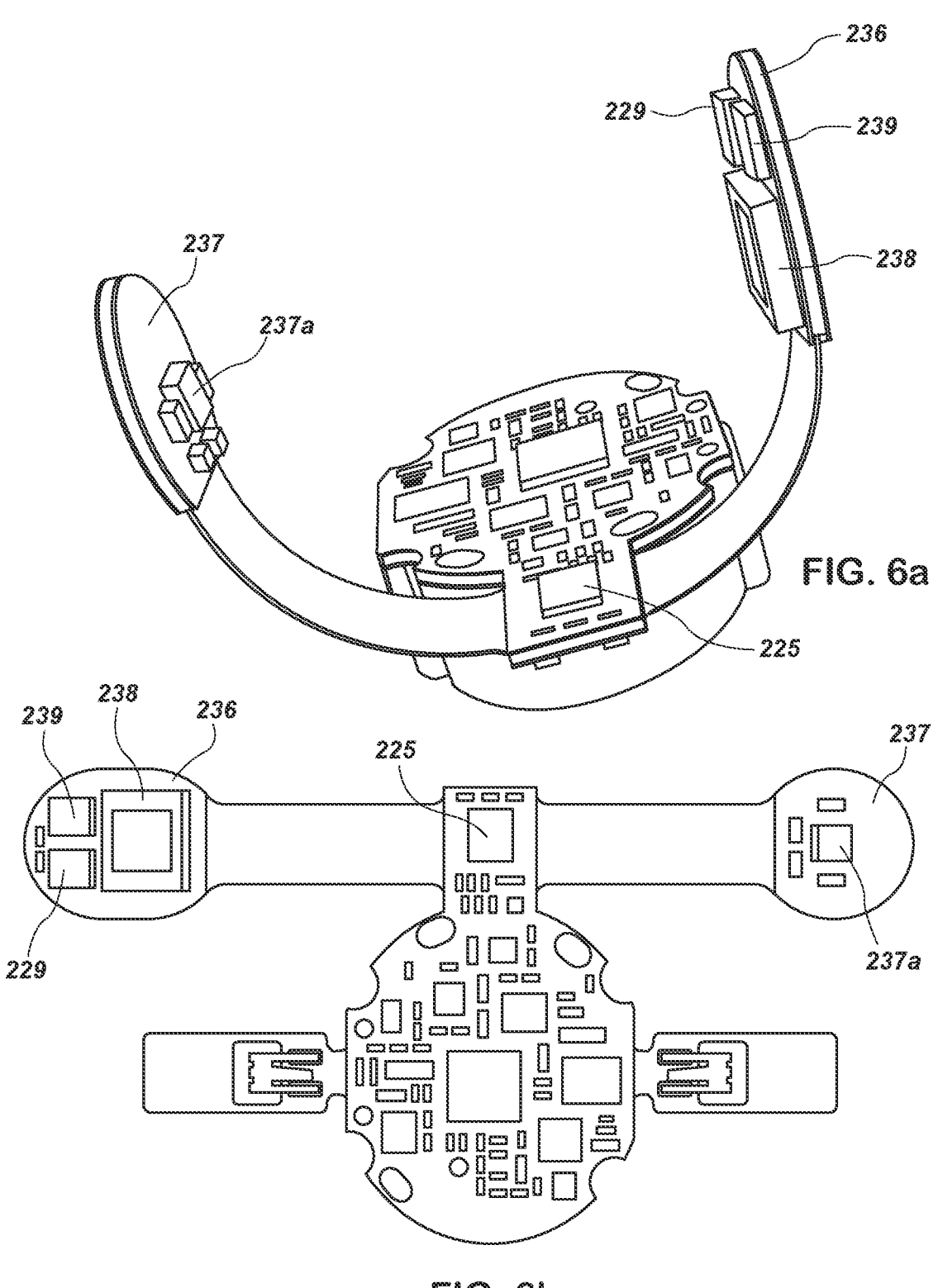
FIG. 6a is an elevated perspective view of a portion of a sensor module in accordance with one aspect of the technology.
FIG. 6b is a top view of a portion of a sensor module in accordance with one aspect of the technology.

In one aspect of the technology, when the sensor module 200 is properly placed on the foot of the infant, sensor assembly 236 will be located about a bottom portion of the foot of the infant, while sensor assembly 237 will be located about a top portion of the foot of the infant or vice versa. Meaning, the sensor assembly 236 may be located on a top portion of the foot while sensor assembly 237 may be located on the bottom portion of the foot. In any event, the sensors are aligned such that light propagated from one sensor is in the field of view of the other sensor. In other words, wavelengths of light propagated by one sensor through the tissue of the subject (i.e., the amount not absorbed by the tissue) is detected by the other sensor. In one aspect, when properly positioned on the foot of the infant, sensor assembly 236 will be positioned directly beneath sensor assembly 237. As seen in FIG. 6, for example, the sensor assembly 236 is facing sensor assembly 237 such that a line of sight is substantially normal to both faces of the respective sensor assemblies. While reference is made herein to sensor assemblies 236, 237 in a general sense, in one aspect of the technology, the sensor assembly 237 is referred to as a transmitter assembly in that it comprises components that transmit or propagate light while sensor assembly 236 is referred to as a receiver assembly in that it comprises components that measure light or other information.

In one aspect of the technology, sensor assembly 236 comprises a photodiode or other photoreceptor 239 configured to detect and measure an amplitude of light and/or measure and detect the amplitude of different wavelengths of light. In an instance where sensor assembly 236 measures both the amplitude and wavelength of light from the sensor (or transmitter) assembly 237, the light propagated from assembly 237 need not be sequential, but may be propagated concurrently. In one aspect, the sensor assembly 236 is coupled to PCB 225 of the sensor module 200 as is sensor assembly 237 such that calculations regarding anticipated or expected absorption rates for specific wavelengths of light may be made. In one aspect of the technology, sensor 237 comprises one or more light-emitting diodes (LEDs) 237a configured to propagate a plurality of discrete wavelengths of light for predetermined periods of time at a predetermined interval. In one aspect, one LED is configured to propagate red light, with wavelength of about 660 nm (or ranging from between 650 nm to 670 nm, 640 nm to 680 nm, or 630 nm to 690 nm for example). A second LED is configured to propagate infrared light having a wavelength of about 940 nm (or ranging from between 930 nm to 950 nm, 920 nm to 960 nm, or 910 nm to 970 nm, for example). Absorption of light at these wavelengths differs significantly between blood loaded with oxygen and blood lacking oxygen. Oxygenated hemoglobin absorbs more infrared light and allows more red light to pass through. Deoxygenated hemoglobin allows more infrared light to pass through and absorbs more red light.

The LEDs (or single LED configured to propagate light at different frequencies) sequence through a cycle of one on, then the other, then both off ranging from about 30 times per second (30 Hz) to about 40 times per second (40 Hz), which allows the photodiode to respond to the red and infrared light separately and also adjust for any ambient light baseline. In another aspect, however, the system cycles through the different light propagation sequence at greater than 140 Hz, 150 Hz, or 160 Hz. The amount of light that is transmitted (i.e., not absorbed by the tissue) is measured by a photodiode 238 on sensor assembly 236, and separate normalized signals are produced for each wavelength. These signals fluctuate in time because the amount of arterial blood that is present increases with each heartbeat. By subtracting the minimum transmitted light from the transmitted light in each wavelength, the effects of other tissues are corrected for, generating a continuous signal for pulsatile arterial blood. The ratio of the red light measurement to the infrared light measurement is then calculated by the processor which represents the ratio of oxygenated hemoglobin to deoxygenated hemoglobin. This ratio is then converted to SpO2 by the processor via a lookup table based on the Beer-Lambert law.

In one aspect of the technology, sensor assembly 237 comprises a third LED configured to propagate green light at a wavelength of 530 nm (ranging from 515 nm to 545 nm, 510 nm to 550 nm, or 505 nm to 555 nm for example) which is also used in connection with the determination of blood oxygen content and heart rate, though the green light may also be used to help determine proper positioning of the device. In one aspect of the technology, the third LED of the sensor assembly 237 is configured to propagate blue light at a wavelength of 460 nm (ranging from 450 nm to 470 nm, 440 nm to 480 nm, or 430 nm to 490 nm, for example). When the sensor module 200 is correctly placed on the foot (or other body part), significantly more blue light will be absorbed by the tissues than red light. This results in a much stronger average signal being received by the photodiode 238 of sensor assembly 236 when the red LED is on than is received when the blue LED is on. If the device is not properly placed on the foot, the average signal being received by the photodiode 238 of sensor assembly 236 will be similar with either the red or blue LEDs on.

In the aspect where sensor assembly 237 also includes a photodiode, a similar comparison would be made between the different values of light that were reflected off of the surface of the foot (or other body part). Meaning, the amount of light reflected from the foot will be different when the sensor module 200 is properly placed and when it is not. While reference is made herein to a third LED, it is understood that in certain aspects of the technology, different wavelengths of light may be propagated from the same light source. Meaning, the first or second LEDs may propagate the blue and/or green light referenced above. It is also understood that the device may be equipped with a fourth LED or more as suits a particular purpose. It is also understood that different wavelengths of light may be used herein to the extent they have different optical characteristics. Meaning, blue light may be mentioned specifically in one aspect of the comparison, but green light may also be used as well as many other wavelengths as they exist on the electromagnetic spectrum so long as their optical characteristics allow for a ratio to be calculated.

In one aspect of the technology, when calculating the amount of light passing through the foot (or other tissue) to the photodiode 238 of sensor assembly 236, the log of the ratio of the amount of received wavelength of light is compared to the amount of propagated light. The difference in the log value between red light and blue light (or other wavelengths of light including infrared wavelengths of light, etc.) will be independent of how thick, reflective, or optically dark the foot is. This allows for a consistent threshold to be used for determining whether the device is placed correctly.

Figure 7:
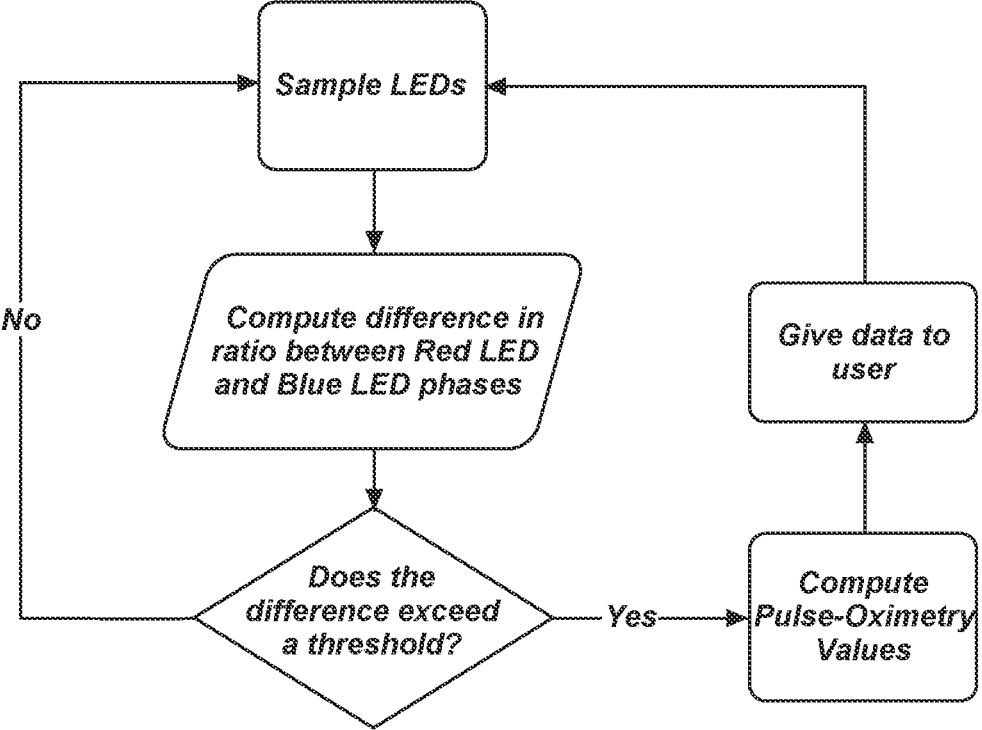
FIG. 7 is a flow diagram in accordance with one aspect of the technology.

With reference generally to the flow diagram of FIG. 7, in one aspect of the technology, the optical loss is calculated by measuring the dBs at the photodiode and taking the log of the current transfer ratio for each wavelength of light used (e.g., blue and red, etc.) as follows:

$$20*\log 10(pd\_current/led\_current)$$

The difference between the dB values for each wavelength is then computed:

$$red\_dB - blue\_dB$$

If red_dB is more than a threshold in dB greater than blue_dB (e.g. 5 dB, 10 dB, 15 dB, etc.) the sensor module 200 is considered to be placed correctly. If it is less than the threshold, the sensor module 200 is not considered to be placed correctly.

In another aspect of the technology, the ratio of blue_ctr to red_ctr is used to determine a threshold for when the sensor module 200 is placed correctly. In this aspect, the terms blue_ctr and red_ctr refer to the current transfer ratio of a particular band or wavelength of light related to current. Specifically, in this aspect, the current transfer ratio refers to the ratio of the collector current (i.e., the current at the photoreceptor 239) at the output side IC to the input current passed to the LED 237a at the input side IF expressed as a percentage. It is defined by the following formula: CTR= (IC/IF)×100(%). In one aspect of the technology, a comparison of CTR_blue to CTR_IR would trigger a threshold alarm if CTR_blue/CTR_IR were greater than 0.4, 0.45, or 0.5

While reference is made to the differences in the blue and red bands of light in this comparison, it is understood that other bands or wavelengths of light may be used for the current transfer ratio comparison. For example, the difference between blue and infrared bands, blue and green bands, etc. can be used to determine proper positioning of the sensor module 200. Additionally, these values may have smoothing filters applied so as to not be overly responsive to noisy measurements. Moreover, while the difference between the log of the current transfer ratio is noted, it is understood that other methods are contemplated for use herein to compare the current transfer ratio between different wavelengths of light without department from the scope of the technology, including, but without limitation, As noted herein, the sensor module 200 can perform many functions, but to ensure the information is correctly gathered from the subject, the sensor module 200 must be correctly placed. If the sensor module 200 detects that it is correctly placed, collected information from one or more sensors is used to seed the algorithms used to detect various functions, such as heart rate, blood-oxygen, etc. If the sensor module 200 is not properly placed, and the algorithms include all of the collected data in the data analysis process, there is a risk of erroneous data calculation.

In another aspect of the technology, sensor assemblies 236 and/or 237 comprise a heat flux sensor 239 which is also used to determine whether a sensor module 200 is properly placed on the foot of the infant. In one aspect of the technology, the heat flux sensor 239 is positioned near the body of the subject to detect the heat emanating from the body. This is preferable over a simple temperature measurement as the temperature of the ambient environment can approximate a subject's temperature and give false positives. Other methods can also produce false positives, such as an infrared (or "IR") proximity detector. IR detectors determine how much IR reflection a surface (i.e., the skin of the subject) produces. An amount of reflected IR back into a photodiode, provides information with respect to the distance a sensor is disposed from the surface of the skin. The amount of IR reflected from the surface of the skin of a subject is effected by the color and texture of the surface. Accordingly, variations in skin color and texture can affect the accuracy of the IR detector method used to make distance measurements.

In one aspect of the technology, a heat flux sensor 239 is used to minimize the effect variations of skin color and texture may have on distance determinations. Advantageously, the variations of skin color and texture are eliminated, but the heat flux sensor 239 also does not require an optical window or line of sight from the sensor 239 to the skin surface to approximate distance values from the sensor to the skin. Rather, the heat flux sensor 239 requires a conductive path for heat flux from the user to the sensor. In one aspect of the technology, sensor assembly 236 comprises a heat flux sensor 239 placed near the photodiode 238. In one aspect, the thermal characteristics of sensor assembly 236 are better than those of sensor assembly 237 as there are, in some aspects of the technology, only passive electronic components in sensor assembly 236 and all are low power components that do not generate a significant amount of heat. In this manner, the heat flux sensor 239 detects heat flux from the body instead of heat generated by electronics components themselves. In another aspect of the technology, the heat flux sensor 239 is located about the sensor assembly 237. In yet another aspect, two heat flux sensors are located on the sensor module, one about sensor assembly 236 and another about sensor assembly 237. In yet another aspect, a heat flux sensor may be located apart from the sensor assemblies 236, 237 but arranged in a manner that the placement of the heat flux sensor is still a measure of the proper placement of sensor assemblies 236 and 237. For example, in one aspect, the heat flux sensor 239 may be disposed about a tab extending away from sensor 236 and/or 237. A temperature sensor 229 may also be located on sensor assembly 236, for example, to provide additional information to confirm the accuracy of heat flux sensor 239.

In one aspect of the technology, the sensor assemblies 236, 237 couple to the PCB 225 by way of an analog front end as shown in FIG. 6. In one aspect of the technology, the heat flux sensor 239 is a low output impedance low voltage output sensor. In this aspect, the signal needs to be amplified before going through an ADC and then finally to the microcontroller. In the microcontroller, the heat flux sensor data is used to seed an algorithm and compared to a database to determine if the heat flux data matches what is expected when the sensor module 200 (and more importantly sensors 236 and 237) is correctly placed about the foot of the infant. In one aspect, the circuit uses a main amplifier for the heat flux sensor and temperature sensor setup in a non-inverting configuration with approximately 214V/V of gain. The heat flux sensor and temperature sensor rout to the microcontroller via an I2C bus. A virtual ground is created so that the heat flux sensor can read heat flux in both a positive and negative direction or into or out of the sensor. The ADC then digitizes the signal and passes this information to the microcontroller for processing.

Figure 8:
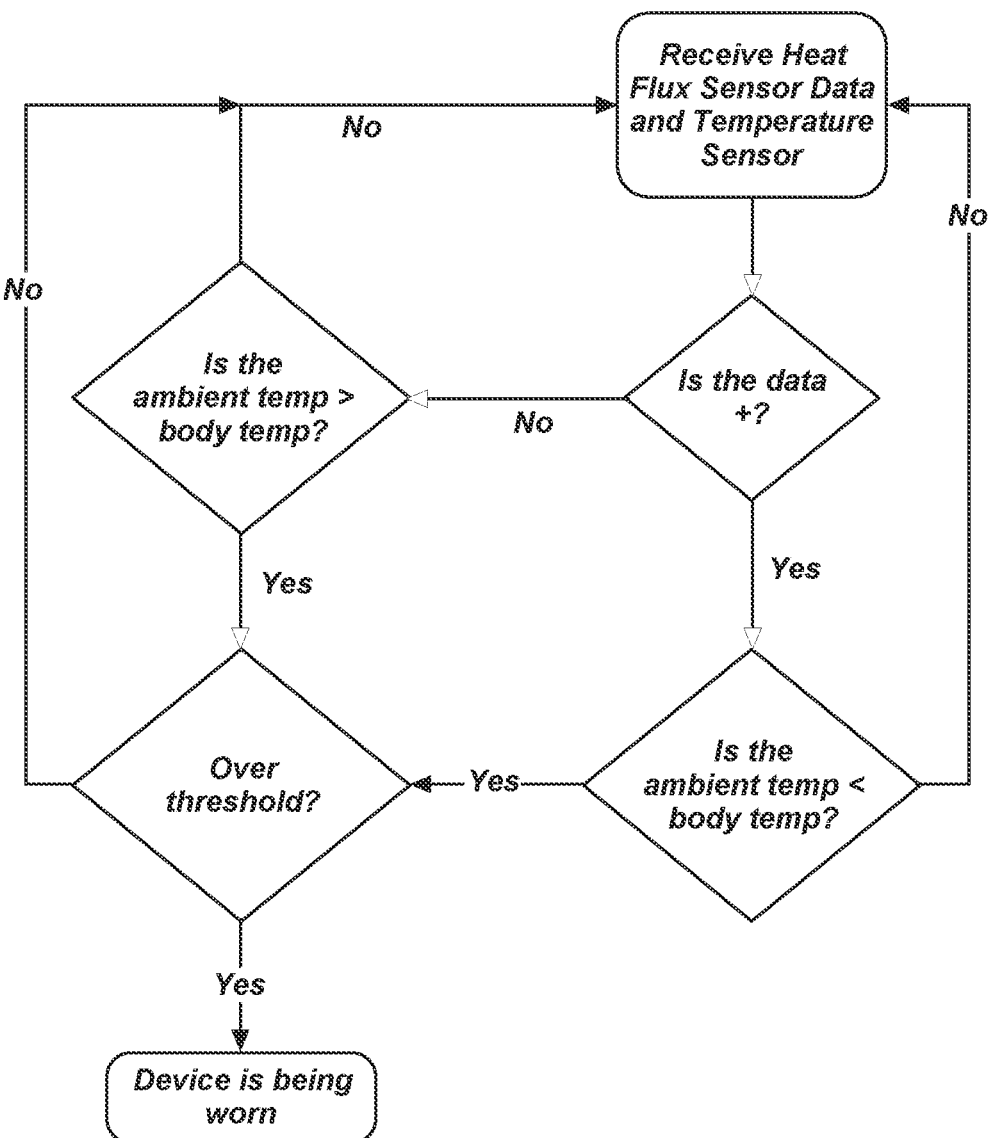
FIG. 8 is a flow diagram in accordance with one aspect of the technology.

The algorithm used to calculate heat flux can vary in complexity depending on how the heat flux is used. In one aspect, a simple algorithm could be used that utilizes a low pass filter with a set threshold, either positive or negative, to know if the sensor is next to a body. In another aspect, the heat flux polarity is analyzed by comparing the ambient temperature through a separate temperature sensor 229 located about the sock or garment 100 or sensor module 200. In one aspect of the technology, once the heat flux placement detector signals that the sensor module 200 is properly positioned, the algorithm processing blood oxygen levels and heart rate are processed with an increased level of confidence. FIG. 8 is a flow diagram demonstrating steps in determining whether the sensor module 200 is properly placed and readings are being properly taken in accordance with one aspect of the technology. In yet another aspect of the technology, data is collected from the temperature sensor 229 and heat flux sensor 239. Once heat flux sensor and/or temperature sensor data is received, it is determined if there is a positive (+) flow of heat coming from the target. If the temperature sensor 229 indicates that the temperature is greater than a predetermined temperature corresponding to the temperature of the subject (e.g., about 98.6 degrees F.), the microcontroller looks for a decrease in the temperature flux measured from flux sensor 238; otherwise the microcontroller looks for an increase in the temperature flux measured from flux sensor 238. If the change in the temperature flux measured from the flux sensor 238 is greater than a predetermined threshold, a signal is generated indicating that the sensor assembly 200 was recently put on by the user. During continued monitoring of data collected by the heat flux sensor 238, if a sudden increase or decrease (e.g., a change greater than 5%, 10%, 15%, or 20% from a baseline within a 100 ms to 1 s period of time) is observed in measured heat flux, a signal is generated indicating that the sensor assembly 200 may not be properly positioned on the subject.

In one aspect of the technology, if it is determined that the device is not properly positioned, a signal is sent that notifies the user of the status of the device. For example, the device may produce an audible or visual cue to the user or it may send a signal to a base station or mobile device indicating to the user that the device is not properly positioned. In another aspect, if the device is not properly positioned, the device will "shut down" or stop taking pulse-oximetry or other data measurements to conserve battery power, until a signal that the device is properly positioned is generated by the device.

The printed circuit board or PCB 225 of the electronics sub-assembly 220 contains memory and programming instructions for storing information used for performing the functions described herein, including, but not limited to delivering a signal to the sensors and record data received from the sensors, propagating light from the lighting source(s) (e.g., LEDs), and making the calculations referencing herein, though calculations and/or memory and instructions may be stored and executed at a remote location, such as on a base station or on a cloud-based system. Memory refers to electronic circuitry that allows information, typically computer data, to be stored and retrieved. Memory can refer to external devices or systems, for example, disk drives or other digital media. Memory can also refer to fast semiconductor storage, for example, Random Access Memory (RAM) or various forms of Read Only Memory (ROM) that are directly connected to the processor. Computer terminals represent any type of device that can access a computer network. Devices such as PDA's (personal digital assistants), cell phones, personal computers, lap top computers, tablet computers, mobile devices, or the like could be used to access information produced by the sensor module. The computer terminals, including mobile devices, may have a display device and one or more input devices. The network may include any type of electronically connected group of computers including, for instance, Internet, Intranet, Local Area Networks (LAN), cloud-based systems, or Wide Area Networks (WAN). In addition, the connectivity to the network may be, for example, remote modem or Ethernet.

The above description provides numerous specific details for a thorough understanding of the embodiments described herein. However, those of skill in the art will recognize that one or more of the specific details may be omitted, or other methods, components, or materials may be used. In some cases, operations are not shown or described in detail. Furthermore, the described features, operations, or characteristics may be combined in any suitable manner in one or more embodiments. It will also be readily understood that the order of the steps or actions described in connection with the embodiments disclosed may be changed as would be apparent to those skilled in the art.

As will be appreciated by one skilled in the art, aspects of the present technology may be embodied as a system, method or used with a computer program product as part of an infant monitoring device. Accordingly, aspects of the present technology may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present technology may take the form of a computer program product embodied in one or more computer readable medium(s) having computer readable program code embodied thereon.

Any combination of one or more computer readable medium(s) may be utilized in recording and reporting the data collected from the device. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, blue tooth, etc., or any suitable combination of the foregoing. Computer program code for carrying out operations for aspects of the present technology may be written in any combination of one or more programming languages, including an object oriented programming language such as Java, Visual Basic, SQL, C++ or the like and conventional procedural programming languages, such as the "C" programming language or similar programming languages. The program code may execute entirely or partly on the device itself, on a user's computer, mobile device, as a stand-alone software package, partly on the user's computer and partly on a remote computer, entirely or partly within a monitor controller, or entirely on the remote computer or server or the monitoring device. In the latter scenario, the remote computer may be connected to the user's mobile device or monitoring device through any type of network, including a local area network (LAN) or a wide area network (WAN), or the connection may be made to an external computer or cloud-based system (for example, through the Internet using an Internet Service Provider).

The foregoing detailed description describes the technology with reference to specific exemplary embodiments. However, it will be appreciated that various modifications and changes can be made without departing from the scope of the present disclosure. The detailed description and accompanying drawings are to be regarded as merely illustrative, rather than as restrictive, and all such modifications or changes, if any, are intended to fall within the scope of the present disclosure as described and set forth herein.

The invention claimed is:

1. A monitoring system, comprising:
a sensing module comprising an enclosure, the enclosure housing an electronics sub-assembly comprising a first sensor assembly and a second sensor assembly; and
one or more processors and computer-readable media having stored thereon executable instructions that when executed by the one or more processors configure the sensing module to:
propagate, from the first sensor assembly, a sequence of light, the sequence of light comprising:
a first wavelength of light for a first predetermined amount of time,
after the first predetermined amount of time, propagate no light for a second predetermined amount of time,
after the second predetermined amount of time, propagate a second wavelength of light for a third predetermined amount of time, and
substantially immediately after the propagation of the second wavelength of light, propagate a third wavelength of light for a fourth predetermined amount of time, wherein the first wavelength of light, the second wavelength of light, and the third wavelength of light all comprise different wavelengths of light,
detect, with the second sensor assembly, light propagated from the first sensor assembly,
calculate a value for the first wavelength by comparing a detected amount of the first wavelength of light detected by the second sensor assembly to a predetermined first amount of the first wavelength of light propagated from the first sensor assembly, calculate a value for the third wavelength by comparing a detected amount of the third wavelength of light detected by the second sensor assembly to a predetermined second amount of the third wavelength of light propagated from the first sensor assembly, calculate a difference between the value for the first wavelength of light and the value for the third wavelength of light, when the difference is less than a threshold value, determine that the sensing module is not placed correctly, and when the difference is equal to or greater than the threshold value, determine that the sensing module is placed correctly.

2. The monitoring system of claim 1, wherein the first wavelength of light ranges from 650 nm to 670 nm and the second wavelength of light ranges from 920 nm to 970 nm.

3. The monitoring system of claim 1, wherein the third wavelength of light is either in a light range of (i) 450 nm to 470 nm or (ii) 515 nm to 545 nm.

4. The monitoring system of claim 1, wherein the first sensor assembly comprises one or more light emitting diodes configured to propagate light to a target.

5. The monitoring system of claim 1, wherein the second sensor assembly comprises one or more photodiodes configured to measure an amount of light propagated from the first sensor assembly.

6. The monitoring system of claim 1, wherein the first sensor assembly comprises one or more light emitting diodes and one or more photodiodes.

7. The monitoring system of claim 6, further comprising a processor with executable instructions to compare the amount of light propagated from the first sensor assembly to the amount of light that is reflected off of a subject.

8. The monitoring system of claim 6, wherein the sensing module further comprises a heat flux sensor, and the one or more processors and the executable instructions further configure the one or more processors to:

based on one or more readings from the heat flux sensor, determine that the sensing module is not placed correctly.

9. The monitoring system of claim 6, wherein the sensing module further comprises a temperature sensor.

10. A method for determining proper placement of a monitoring device on a subject, comprising:

placing a monitoring device in contact with a skin of a subject, the monitoring device comprising a sensing module having an electronics sub-assembly with a first sensor assembly and a second sensor assembly;

propagating, from the first sensor assembly, a first wavelength of light for a first predetermined amount of time;

after the first predetermined amount of time, propagating, from the first sensor assembly, no light for a second predetermined amount of time;

after the second predetermined amount of time, propagating, from the first sensor assembly, a second wavelength of light for a third predetermined amount of time;

substantially immediately after the propagation of the second wavelength of light, propagating, from the first sensor assembly, a third wavelength of light for a fourth predetermined amount of time, wherein the first wavelength of light, the second wavelength of light, and the third wavelength of light all comprise different wavelengths of light;

detecting, with the second sensor assembly, light propagated from the first sensor assembly;

calculating a value for the first wavelength by comparing a detected amount of the first wavelength of light detected by the second sensor assembly to a predetermined first amount of the first wavelength of light propagated from the first sensor assembly;

calculating a value for the third wavelength by comparing a detected amount of the third wavelength of light detected by the second sensor assembly to a predetermined second amount of the third wavelength of light propagated from the first sensor assembly;

calculating a difference between the value for the first wavelength of light and the value for the third wavelength of light;

when the difference is less than a threshold value, determining that the sensing module is not placed correctly;

and when the difference is equal to or greater than the threshold value, determining that the sensing module is placed correctly.

11. The method of claim 10, wherein the first wavelength of light ranges from 450 nm to 470 nm and the second wavelength of light ranges from 920 nm to 970 nm.

12. The method of claim 10, wherein the first wavelength of light ranges from 650 nm to 680 nm and the second wavelength of light ranges from 515 nm to 545 nm.

13. The method of claim 10, wherein the first sensor assembly comprises one or more light emitting diodes configured to propagate light to a target.

14. The method of claim 10, wherein the second sensor assembly comprises one or more photodiodes configured to measure an amount of light propagated from the first sensor assembly.

15. The method of claim 10, wherein the first sensor assembly comprises one or more light emitting diodes and one or more photodiodes.

16. The method of claim 15, further comprising comparing the amount of light propagated from the first sensor assembly to the amount of light that is reflected off of a subject.

17. The method of claim 15, further comprising:

based on one or more readings from a heat flux sensor, determining that the sensing module is not placed correctly.

18. The method of claim 10, wherein the sensing module further comprises a temperature sensor.

* * * * *